United States Patent
Ricker et al.

(10) Patent No.: US 10,327,824 B2
(45) Date of Patent: Jun. 25, 2019

(54) PATELLA FRACTURE REDUCTION PLATES

(71) Applicant: Biomet Manufacturing, LLC, Warsaw, IN (US)

(72) Inventors: Lauren Ricker, Warsaw, IN (US); Daniel S Horwitz, Danville, PA (US); Roy Sanders, Warsaw, IN (US); Dan Dziadosz, Tampa, FL (US); Peter Giannoudis, Leeds (GB)

(73) Assignee: Biomet Manufacturing, LLC, Warsaw, IN (US)

( * ) Notice: Subject to any disclaimer, the term of this patent is extended or adjusted under 35 U.S.C. 154(b) by 249 days.

(21) Appl. No.: 15/294,528

(22) Filed: Oct. 14, 2016

(65) Prior Publication Data

US 2017/0105775 A1    Apr. 20, 2017

Related U.S. Application Data

(60) Provisional application No. 62/241,863, filed on Oct. 15, 2015.

(51) Int. Cl.
*A61B 17/80* (2006.01)
*A61B 17/17* (2006.01)

(52) U.S. Cl.
CPC ...... *A61B 17/8061* (2013.01); *A61B 17/1767* (2013.01); *A61B 17/8085* (2013.01)

(58) Field of Classification Search
CPC . A61B 17/80; A61B 17/8052; A61B 17/8057; A61B 17/8061; A61B 17/8085
USPC .................. 606/70, 71, 280–299
See application file for complete search history.

(56) References Cited

U.S. PATENT DOCUMENTS

| | | | | |
|---|---|---|---|---|
| 4,923,471 A | * | 5/1990 | Morgan | A61B 17/8085 606/285 |
| 5,468,242 A | * | 11/1995 | Reisberg | A61B 17/8085 606/151 |
| 5,690,631 A | * | 11/1997 | Duncan | A61B 17/8085 606/281 |
| 5,718,705 A | * | 2/1998 | Sammarco | A61B 17/8085 606/260 |
| 5,766,176 A | * | 6/1998 | Duncan | A61B 17/8085 606/281 |

(Continued)

FOREIGN PATENT DOCUMENTS

| AU | 2016337382 | 5/2018 |
|---|---|---|
| CN | 108366803 | 8/2018 |

(Continued)

OTHER PUBLICATIONS

"Australian Application Serial No. 2016337382, Subsequent Examiners Report dated Sep. 5, 2018", 3 pgs.

(Continued)

*Primary Examiner* — Eric S Gibson
(74) *Attorney, Agent, or Firm* — Schwegman Lundberg & Woessner, P.A.

(57) ABSTRACT

Plates for patella fracture reduction and fracture reduction devices are described. More particularly plates and devices for patella reduction that are universally fit to a front surface or perimeter of a patella and include a plurality of attachment holes disposed therein for receiving a fastener. In some embodiments, the plates include removable tab members.

24 Claims, 12 Drawing Sheets

(56) References Cited

U.S. PATENT DOCUMENTS

| | | | | |
|---|---|---|---|---|
| 5,814,048 | A * | 9/1998 | Morgan | A61B 17/8085 606/283 |
| 5,853,413 | A * | 12/1998 | Carter | A61B 17/8061 606/281 |
| 6,123,709 | A * | 9/2000 | Jones | A61B 17/1728 606/280 |
| 6,348,052 | B1 * | 2/2002 | Sammarco | A61B 17/8085 606/284 |
| 7,335,204 | B2 * | 2/2008 | Tornier | A61B 17/8061 606/280 |
| 7,935,126 | B2 * | 5/2011 | Orbay | A61B 17/1728 606/101 |
| 8,118,846 | B2 * | 2/2012 | Leither | A61B 17/8057 606/280 |
| 8,182,517 | B2 * | 5/2012 | Sixto, Jr. | A61B 17/8061 606/280 |
| 8,337,533 | B2 * | 12/2012 | Raines | A61B 17/8057 606/284 |
| 8,403,968 | B2 * | 3/2013 | Rabiner | A61B 17/8061 606/192 |
| 8,551,143 | B2 * | 10/2013 | Norris | A61B 17/8061 606/280 |
| 8,603,091 | B2 * | 12/2013 | Lutz | A61B 17/8066 606/281 |
| 8,894,693 | B2 * | 11/2014 | Petit | A61B 17/74 606/280 |
| 9,517,097 | B2 * | 12/2016 | Rise | A61B 17/8085 |
| 9,775,657 | B2 * | 10/2017 | Bernstein | A61B 17/808 |
| 10,045,799 | B2 * | 8/2018 | Montello | A61B 17/701 |
| 10,080,599 | B2 * | 9/2018 | Caldarella | A61B 17/809 |
| 2002/0173854 | A1 | 11/2002 | Amrich | A61B 17/8085 623/23.53 |
| 2004/0210220 | A1 * | 10/2004 | Tornier | A61B 17/8061 606/284 |
| 2005/0261780 | A1 * | 11/2005 | Heino | A61B 17/8085 623/23.51 |
| 2005/0273104 | A1 * | 12/2005 | Oepen | A61B 17/8085 606/285 |
| 2006/0085000 | A1 * | 4/2006 | Mohr | A61B 17/8076 606/281 |
| 2006/0235397 | A1 * | 10/2006 | Sanders | A61B 17/8061 606/280 |
| 2007/0233111 | A1 * | 10/2007 | Orbay | A61B 17/1728 606/286 |
| 2009/0105717 | A1 * | 4/2009 | Bluechel | A61B 17/8061 606/280 |
| 2009/0204121 | A1 | 8/2009 | Cavallazzi et al. | |
| 2011/0144699 | A1 * | 6/2011 | Fallin | A61B 17/80 606/286 |
| 2013/0090694 | A1 * | 4/2013 | Norris | A61B 17/8061 606/281 |
| 2014/0058510 | A1 * | 2/2014 | Appenzeller | A61F 2/28 623/16.11 |
| 2014/0309700 | A1 * | 10/2014 | Ng | A61B 17/1728 606/281 |
| 2014/0316472 | A1 * | 10/2014 | Rise | A61B 17/8085 606/281 |
| 2015/0142064 | A1 * | 5/2015 | Perez | A61B 17/8085 606/284 |
| 2016/0192970 | A1 * | 7/2016 | Dayton | A61B 17/8085 606/281 |
| 2016/0361101 | A1 * | 12/2016 | Moctezuma de la Barrera | A61B 90/10 |
| 2017/0065315 | A1 * | 3/2017 | Helfet | A61B 17/8061 |
| 2017/0105775 | A1 * | 4/2017 | Ricker | A61B 17/1767 |
| 2017/0209194 | A1 * | 7/2017 | Ricker | A61B 17/8061 |

FOREIGN PATENT DOCUMENTS

| | | |
|---|---|---|
| JP | 2018531137 A | 10/2018 |
| WO | 2017041091 | 3/2017 |
| WO | 2017066682 | 4/2017 |

OTHER PUBLICATIONS

"Australian Application Serial No. 2016337382, First Examination Report dated Jul. 20, 2018", 5 pgs.

"Application Serial No. PCT/US2016/057193, Invitation to Pay Add'l Fees and Partial Search Report dated Jan. 20, 2017", 6 pgs.

"International Application Serial No. PCT/US2016/057193, International Search Report dated Mar. 13, 2017", 7 pgs.

"International Application Serial No. PCT/US2016/057193, Written Opinion dated Mar. 13, 2017", 8 pgs.

"International Application Serial No. PCT US2016 057193, International Preliminary Report on Patentability dated Apr. 26, 2018", 10 pgs.

"European Application Serial No. 167847615, Response filed Dec. 19, 2018 to Communication Pursuant to Rules 161(2) and 162 EPC dated Jun. 16, 2018", 16 pgs.

"Australian Application Serial No. 2016337382, Subsequent Examiners Report dated Dec. 4, 2018", 3 pgs.

\* cited by examiner

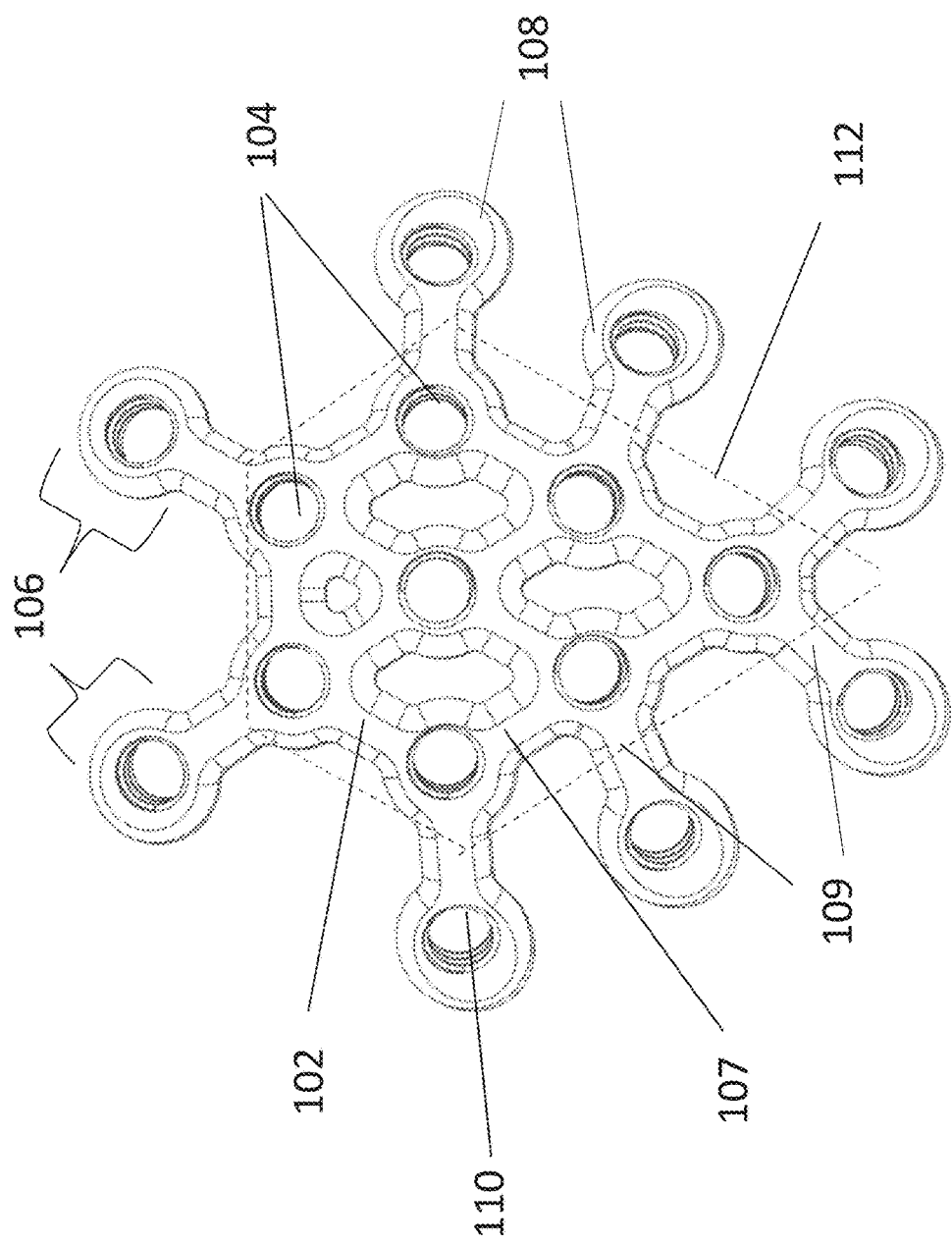

PATELLA FRACTURE REDUCTION PLATES

PRIORITY APPLICATIONS

This application claims the benefit of priority to U.S. Provisional Application Ser. No. 62/241,863, filed Oct. 15, 2015, the content of which is incorporated hereby by reference in its entirety.

BACKGROUND

Fracture reduction devices are known in the art. For long bones, such as the femur, tibia, and fibula, fractures can potentially be reduced using plating systems. For bony areas where the bone includes curvature in multiple axes, and areas where the skin is especially taut to the bone, use of plating systems can be challenging. In such bony areas, such as the patella, other reduction methods have been employed. One such method or system includes high tension mesh plates. Another approach used in the prior art includes wiring or cord systems. In the case of mesh apparatuses, the systems generally require the surgeon to cut the mesh plate to size and fit the mesh for a give patient's patella. Wiring and cabling systems generally require the surgeon to route the wires or cables through channels created in the patella, and/or require the surgeon to wrap the wire or cable around at least a portion of the patella.

SUMMARY

This section provides a general summary of the disclosure, and is not a comprehensive disclosure of its full scope or all of its features.

The present inventors have recognized, among other things, that a problem to be solved is providing a fracture reduction system for the patella that does not require time to individually fit the system for individual patients before or during operation. It would also be desirable to have a system that does not require wire in order to create tension across a fracture, while still maintaining a low profile solution. The present disclosure can help provide a solution to these problems with a strong, flexible plate that is generally a universal fit for patellas of various patients. The system further can provide a solution by utilizing a monolithic plate that does not require the use of wires in order to reduce the fracture (though wires can be used with the presently described system where appropriate and desirable).

The present disclosure includes a first device for patella fracture reduction. The device can include a patellar plate body formed from a monolithic material. The patellar plate body can comprise a central portion and a peripheral portion at least partially surrounding the central portion. The central portion can include a plurality of plate attachment holes disposed therein. The peripheral portion can comprise a plurality of tabs. Each of the plurality of tabs can be coupled to the central portion via a connector portion that is less than about 80% of a plate thickness of the patellar plate body. Each tab can include a tab attachment hole disposed therein. Each tab can be selectively detachable from the patellar plate body. The patellar plate body can be contoured to fit substantially any patella.

The present disclosure includes a second device for patella fracture reduction. The fracture reduction device can include a curved perimeter plate contoured to a perimeter of substantially any patella. The curved perimeter plate can define a plate length between a first end and a second end thereof that extends along at least a portion of the perimeter of a patella. The curved perimeter plate can include a plurality of connection regions positioned along the plate length and a plurality of securing regions positioned along the plate length. At least some of the connection regions can be positioned between two adjacent securing regions. Each securing region can include an attachment hole disposed therein.

The present disclosure further includes systems comprising a patellar plate body and a curved perimeter plate. Such systems can further comprise at least one guide insert removably disposed in at least one of a patellar plate attachment hole, a tab attachment hole, and a perimeter plate attachment hole.

Further areas of applicability will become apparent from the description provided herein. The description and specific examples in this summary are intended for purposes of illustration only and are not intended to limit the scope of the present disclosure.

DESCRIPTION OF THE DRAWINGS

The drawings described herein are for illustrative purposes only of selected embodiments and not all possible implementations, and are not intended to limit the scope of the present disclosure.

FIG. 1A illustrates a top view of a plate for patella fracture reduction, in accordance with at least one example of the present disclosure.

DETAILED DESCRIPTION

Example embodiments will now be described more fully with reference to the accompanying drawings.

Figure 1B:
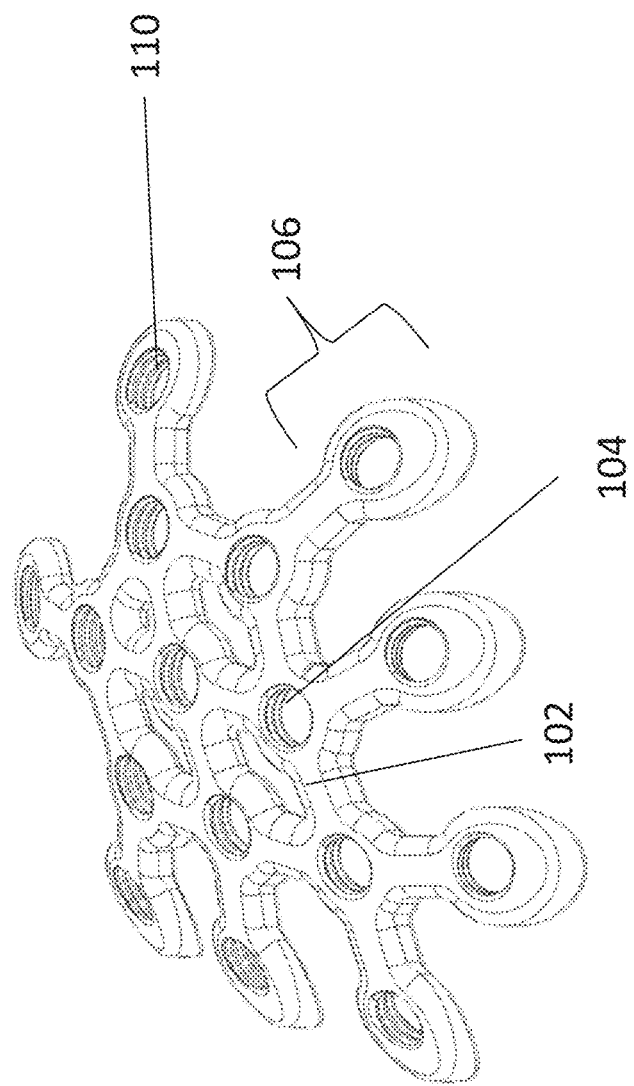
FIG. 1B illustrates a perspective view of a plate for patella fracture reduction, in accordance with at least one example of the present disclosure.
Figure 1C:
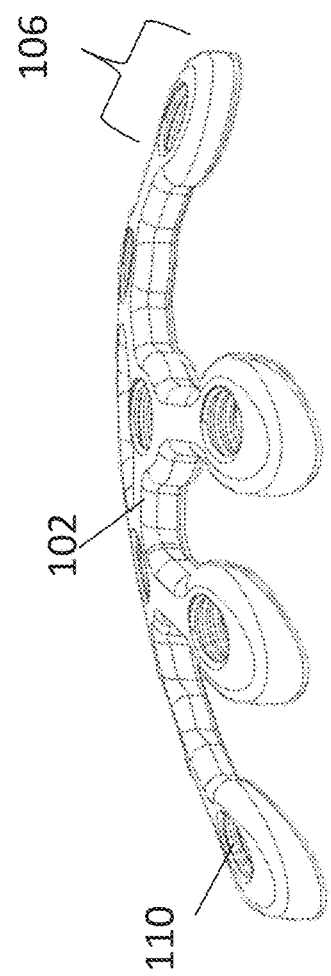
FIG. 1C illustrates a side view of a plate for patella fracture reduction, in accordance with at least one example of the present disclosure.

The present disclosure provides for devices and systems for reducing fractures of the patella including plates. FIGS. 1A-1C illustrate top, perspective and side views of one exemplary plate for patella fracture reduction according to the present disclosure. Plate 100 can include a patellar plate body 102. Patellar plate body 102 can be, in some examples, contoured to conform to a curved surface of substantially any patella and can extend across at least one fracture in the patella. Alternatively, or additionally, plate body 102 can extend across two, three or more fractures on the patella in close proximity to one another. Patellar plate body 102 can be formed from a monolithic material and, additionally or alternatively, can comprise a central portion 107 and a peripheral portion 108 at least partially surrounding the central portion 107. The central portion 107 can include a plurality of plate attachment holes 104 disposed therein. The plate attachment holes 104 can receive a securing element, such as, for example and without limitation, a locking screw, a non-locking screw, and the like.

The peripheral portion 108 of the plate 100 can comprise a plurality of selectively removable tabs 106. Each tab 106 can be coupled to the central portion 107 via a connector portion 109 that can have a thickness that is less than about 80% of a plate thickness of the patellar plate body 102. As a result of the reduced thickness, the tab can be more easily removed. At least some of tabs 106 can include a tab attachment hole 110 disposed therein. Each tab 106 can be selectively detached by, for example and without limitation, bending, deformation, and the like. Each tab attachment hole 110 can receive a securing element in the same fashion as attachment holes 104. In any one or combination of the cases that a tab 106 is not filled with a securing element, poses no benefit, causes overhang, exceeds the surface of the bone, etc., the surgeon can remove the tab member 106. Tab members 106 can be cleanly removed using a few bending cycles or clipping the tab members off with, e.g., plate cutters or a wire cutter.

Plate attachment holes 104 and tab attachment holes 110 can be sized and shaped to receive a securing element in order to secure at least a portion of the plate 100 to the surface of the patella. As shown in FIG. 1 and in other figures herein, any one of the attachment holes can be round, such as circular or oval, although other shapes (e.g., square, hexagonal, etc.) are also contemplated.

Patellar plate body 102 can comprise any number of suitable shapes. In an example, as illustrated in FIG. 1A, plate body 102 can comprise a pentagonal shape (as illustrated by dashed line pentagon 112). In another example, the plate body 102 can have the shape of an upside-down pear or a tear. In another example, the patellar plate body can be sized and shaped in a horizontal and vertical direction, and, additionally, or alternatively, three-dimensionally contoured to fit a patella and, more particularly, universally fit any patella. Patellar plate body 102 can also include any suitable number of plate attachment holes 104 and tab attachment holes 110 (collectively referred to as "attachment holes") necessary to sufficiently secure the plate 100 to the patella and aid in reducing a fracture of the patella. In various examples, the plate body 102 can include at least four attachment holes, at least six attachment holes, at least eight attachment holes, at least ten attachment holes, or more. Attachment holes 104, 110 can accept a securing element that can have a diameter of between about 2.0 mm and about 3.0 mm. In an example, attachment holes 104 can accept a 2.5 mm screw. The securing element can be any suitable fastening member, such as a locking screw, a non-locking screw, or the like. Patellar plate body 102 can be, in an example, made of a material that is moldable to a curved shape but also strong. For example, plate body 102 can be made of titanium or a titanium alloy. In an example, the plate 100 can be monolithic and both the central portion 107 and the peripheral portion 108 can be titanium or a titanium alloy.

Figure 2:
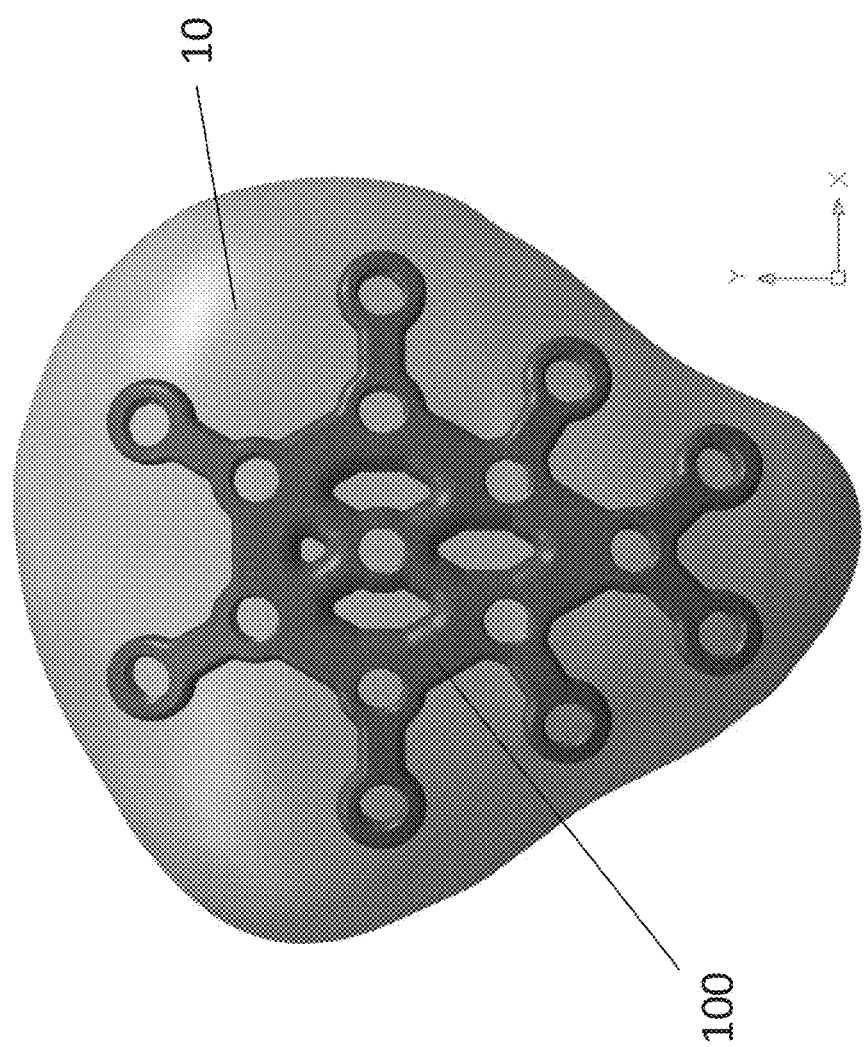
FIG. 2 illustrates a front view of a plate for patella fracture reduction positioned on the surface of a patella, in accordance with at least one example of the present disclosure.

Patellar plate body 102 can have a low profile such that it does not extend a great distance away from the surface of the patella after implantation. In various examples, plate body 102 can have a thickness of less than about 3 mm, less than about 2 mm thick, or less than about 1.6 mm thick. An illustration of plate 100 positioned over the front surface of a patella 10 is provided in FIG. 2.

Figure 3A:
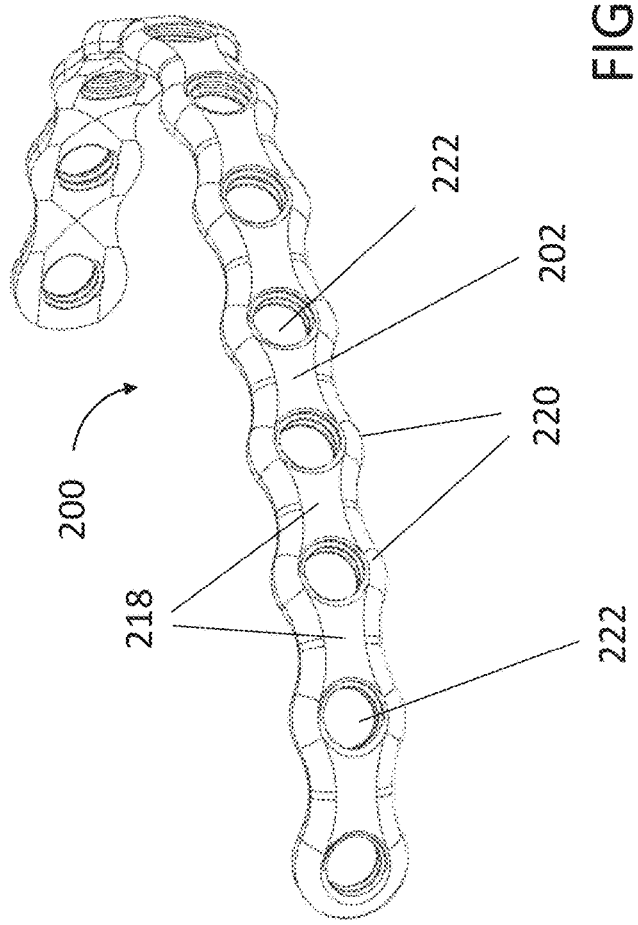
FIG. 3A illustrates a perspective view of a fracture reduction device, in accordance with at least one example of the present disclosure.
Figure 3B:
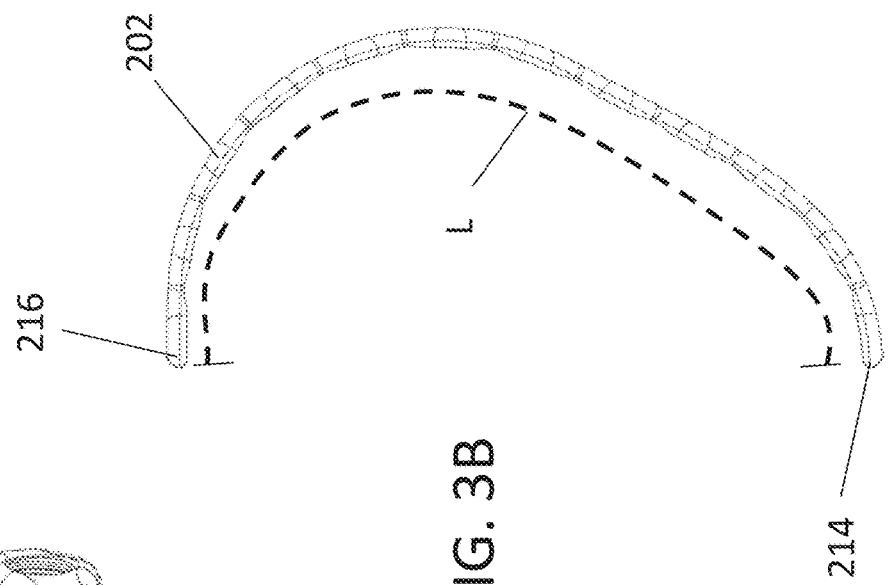
FIG. 3B illustrates a top view of a fracture reduction device, in accordance with at least one example of the present disclosure.

In another example illustrated in FIGS. 3A-3B, the present disclosure relates to a second fracture reduction device. Fracture reduction device 200 can comprise a curved perimeter plate 202 that can be, in various examples, contoured to a perimeter of substantially any patella. The curved perimeter plate 202 can define a plate length L between a first end 214 and a second end 216 thereof that extends along at least a portion of the perimeter of a patella. The plate 202 can comprise a plurality of connection regions 218 that can be positioned along the plate length L and a plurality of securing regions 220 positioned along the plate length. At least some (or potentially all) of the connection regions 218 can be positioned between two adjacent securing regions 218. Each securing region 220 can include an attachment hole 222 disposed therein. As with patellar plate body 102 above, the curved perimeter plate 202 can have a low profile, e.g., the plate can have a thickness of less than 3.0 mm, less than 2.0 mm, or less than 1.6 mm.

Figure 4:
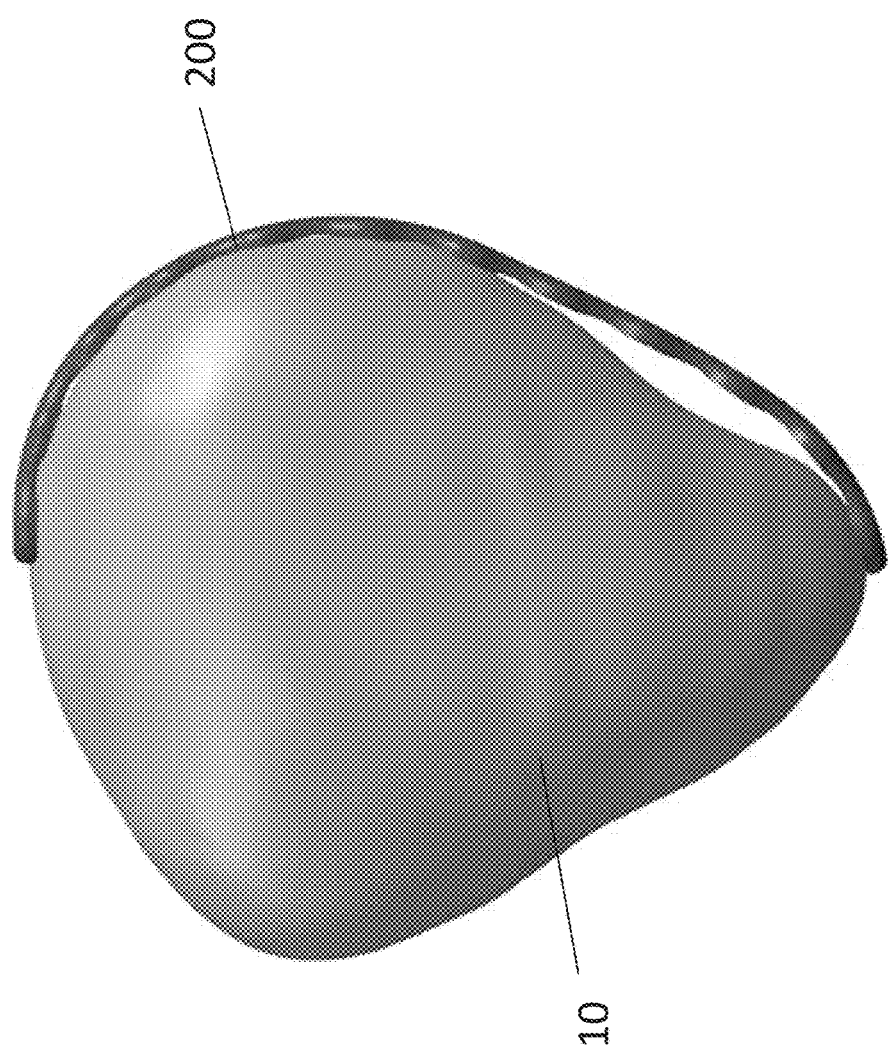
FIG. 4 illustrates a front view of a patella with a fracture reduction device positioned on the perimeter of a patella, in accordance with at least one example of the present disclosure.
Figure 5:
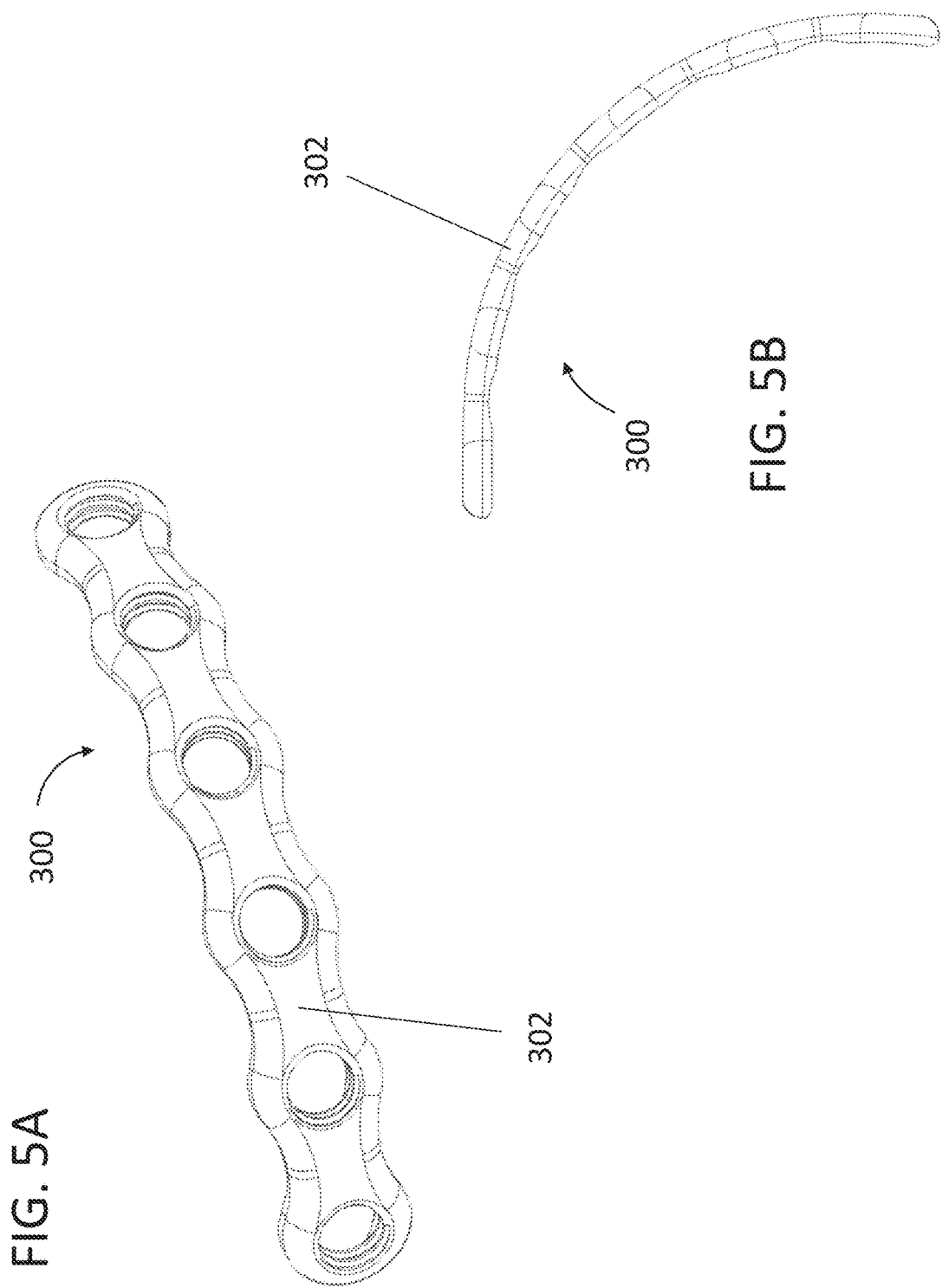
FIG. 5A illustrates a perspective of a fracture reduction device, in accordance with at least one example of the present disclosure.
FIG. 5B illustrates a top view of a fracture reduction device, in accordance with at least one example of the present disclosure.
Figure 6:
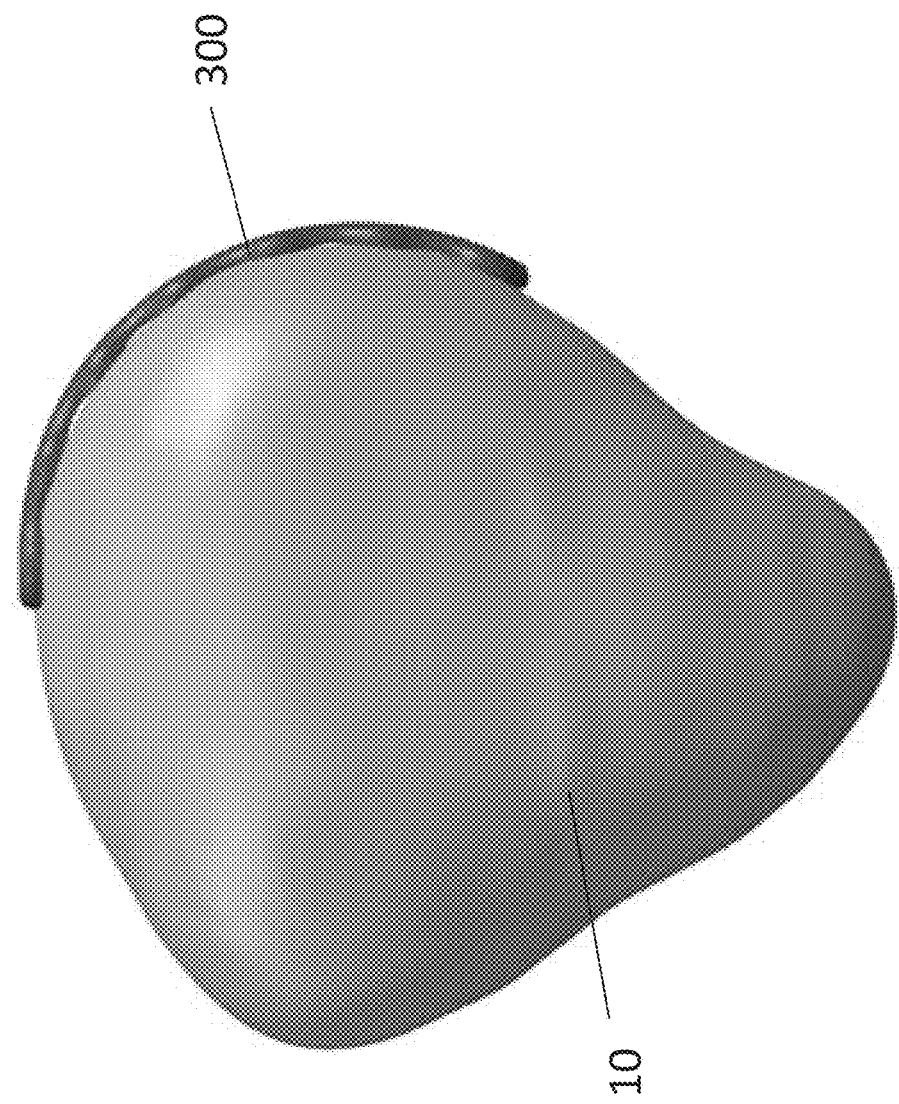
FIG. 6 illustrates a front view of a patella with a fracture reduction device positioned on the perimeter of the patella, in accordance with at least one example of the present disclosure.

In an example illustrated in FIGS. 3A and 3B, the curved perimeter plate 202 can be configured to extend along greater than about one-third of the perimeter of the patella and less than about two-thirds of the perimeter of the patella. For example, the plate 202 can extend along approximately one-half of the perimeter of the patella. An example of a half-perimeter fracture device 200 positioned on the perimeter of a patella 10 is illustrated in FIG. 4. Alternatively, as illustrated with fracture reduction device 300 of FIGS. 5A and 5B, a curved perimeter plate 302 can extend along greater than about one-fifth of the perimeter of the patella and less than about one-third of the perimeter of the patella. For example plate 302 can extend along approximately one-quarter of the perimeter of the patella. An example of a quarter-perimeter fracture device 300 positioned on the perimeter of a patella 10 is illustrated in FIG. 6.

One benefit of all presently described fracture reduction devices is that the devices can be universal to substantially any patella and such that they are not left/right, top/bottom side, or medial/lateral specific. For example, the curvature of the devices can be such that they can generally be positioned on either the medial or lateral side of the patella, and, with regard to the perimeter plates, on the top side or bottom side of the patella along the perimeter.

Returning to FIGS. 3A and 3B, as with the example described in FIGS. 1A-1C, the attachment holes 222 of curved perimeter plate 202 can accept a securing device, such as a screw, that can have a diameter of between about 2.0 mm and about 3.0 mm. In an example, the attachment holes 222 can accept a screw having a diameter of 2.5 mm. The curved perimeter plate 202 can include at least four attachment holes, at least six attachment holes, at least eight attachment holes, or more. Curved perimeter plate 202 can be, in an example, made of a material that is moldable to a curved shape but also strong. For example, curved perimeter plate 202 can be made of titanium or a titanium alloy.

Figure 7A:
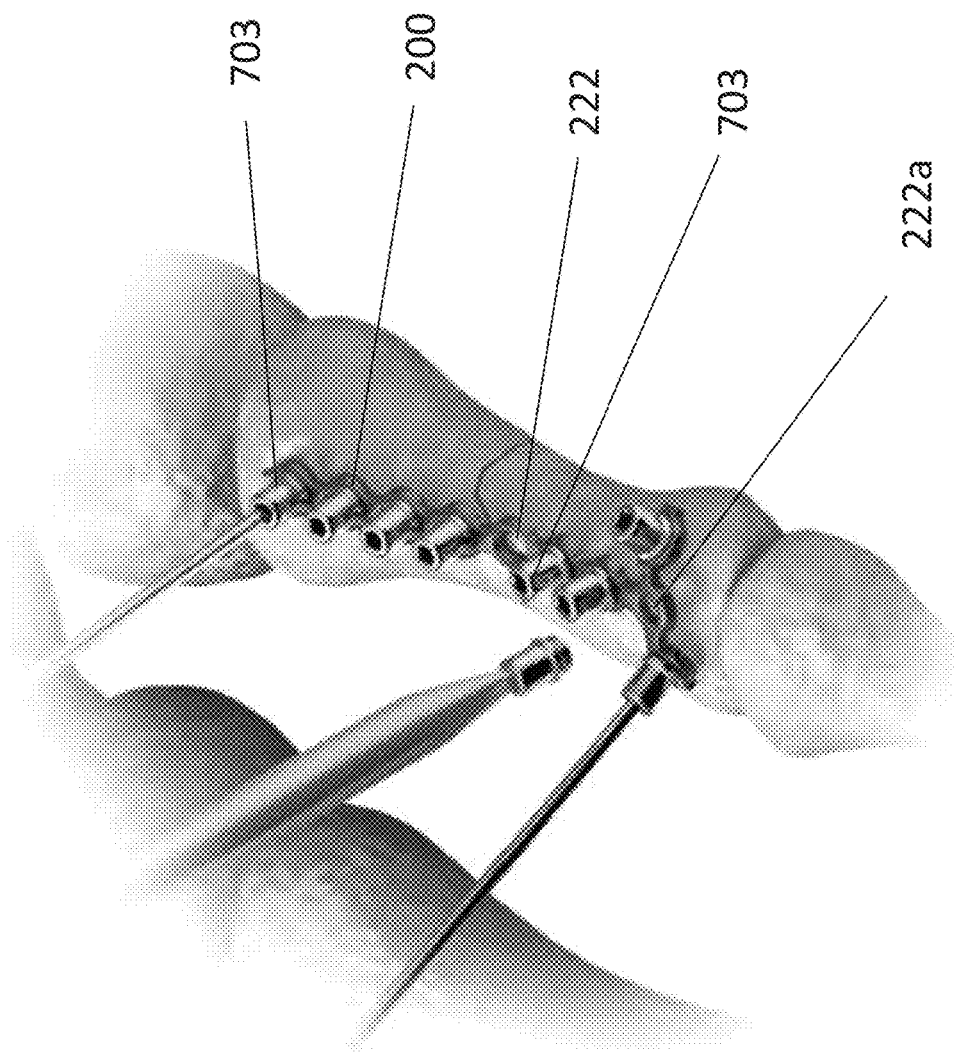
FIGS. 7A-7B provide perspective views of a fracture reduction device with alignment guides, in accordance with at least one example of the present disclosure.
Figure 7B:
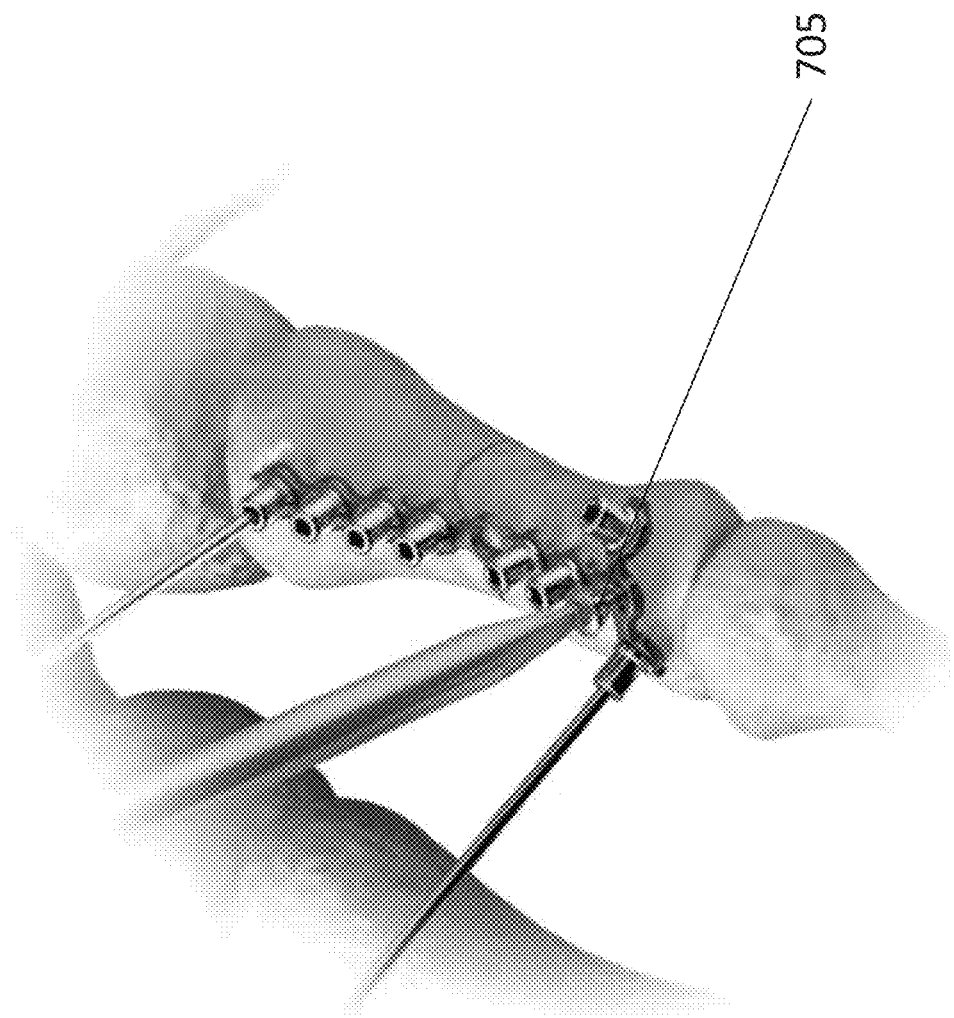
Figure 7C:
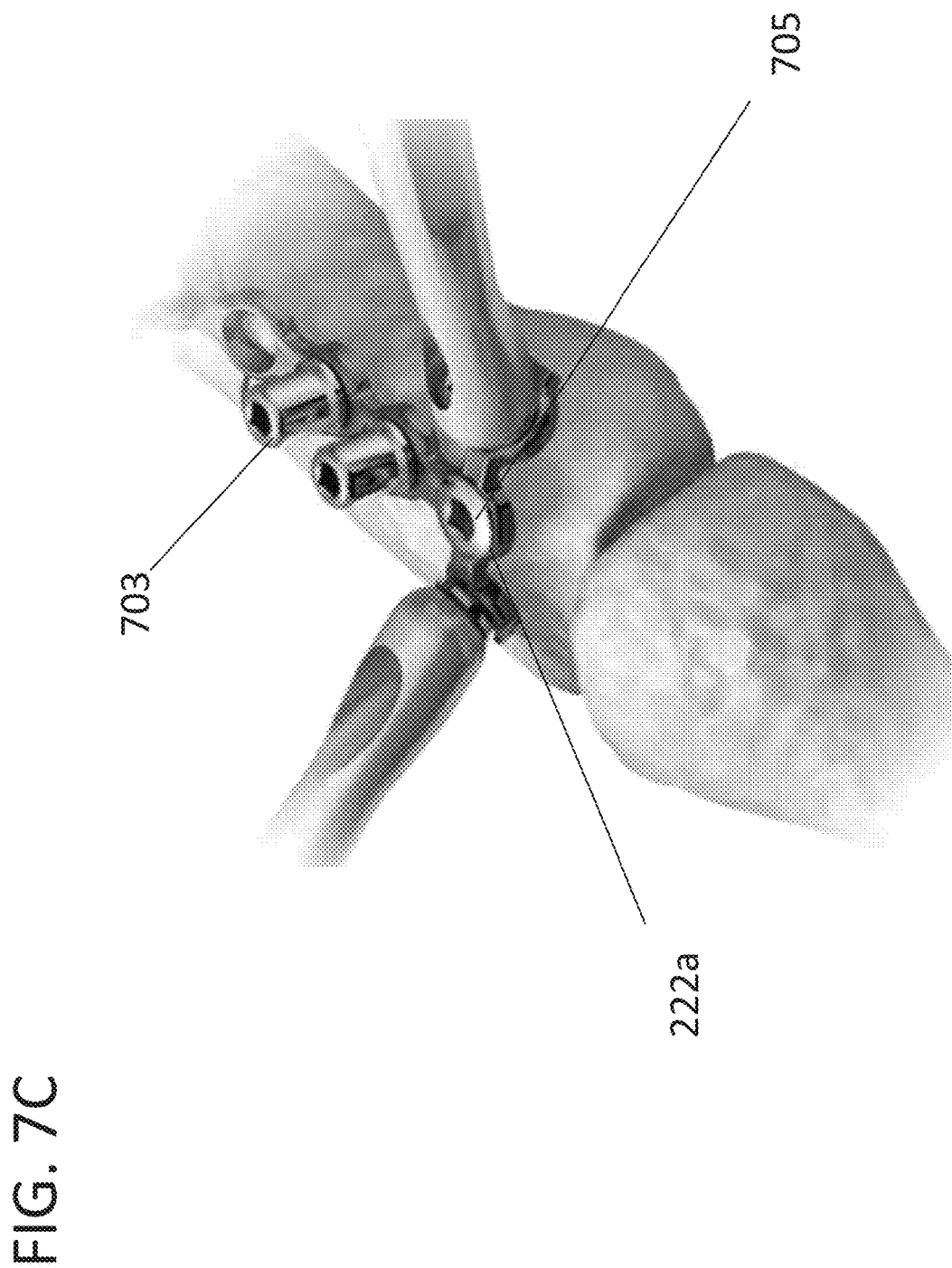
FIG. 7C illustrates a close-up view of a fracture reduction device with alignment guides and a securing element, in accordance with at least one example of the present disclosure.

In various examples, any of the presently described fracture reduction devices can be used with a guide system that can aid in accurate placement of the plate 102, 202 on the patella. An example of a guide system is illustrated in FIGS. 7A-7C. Attachment holes 222 of fracture reduction device 200 can receive guide inserts 703. Guide inserts 703 can be placed into attachment holes 222 prior to the securing element being inserted through the attachment holes. The guide inserts 703 can also define a trajectory for the securing element through the attachment hole. Once the appropriate alignment of the fracture device 200 has been achieved relative to the patella, the guide inserts 703 can be removed. After a given guide insert 703 is removed, a corresponding securing element can be inserted into the attachment hole 703 in order to securely affix the fracture device 200 to the patella. FIG. 7A illustrates a first exemplary guide insert 703a being removed from an attachment hole 222. FIG. 7B illustrates a next step in which a securing element 705 can be inserted into the first attachment hole 222a after the first guide insert has been removed from the hole. The other guide inserts 703 can be left in respective attachment holes 222 during insertion of securing devices into adjacent attachment holes (e.g. 222a) in order to ensure that the fracture device remains appropriately positioned. FIG. 7C illustrates the construction with securing element 7505 fully inserted through attachment hole 222 and into the patella. Though shown in FIGS. 7A-7C with respect to fracture reduction device 200 configured for use on the perimeter of the patella, the plate 100 of FIGS. 1A-1C can also be designed such that attachment holes 104 are configured to receive guide inserts of the type described herein.

Figure 8A:
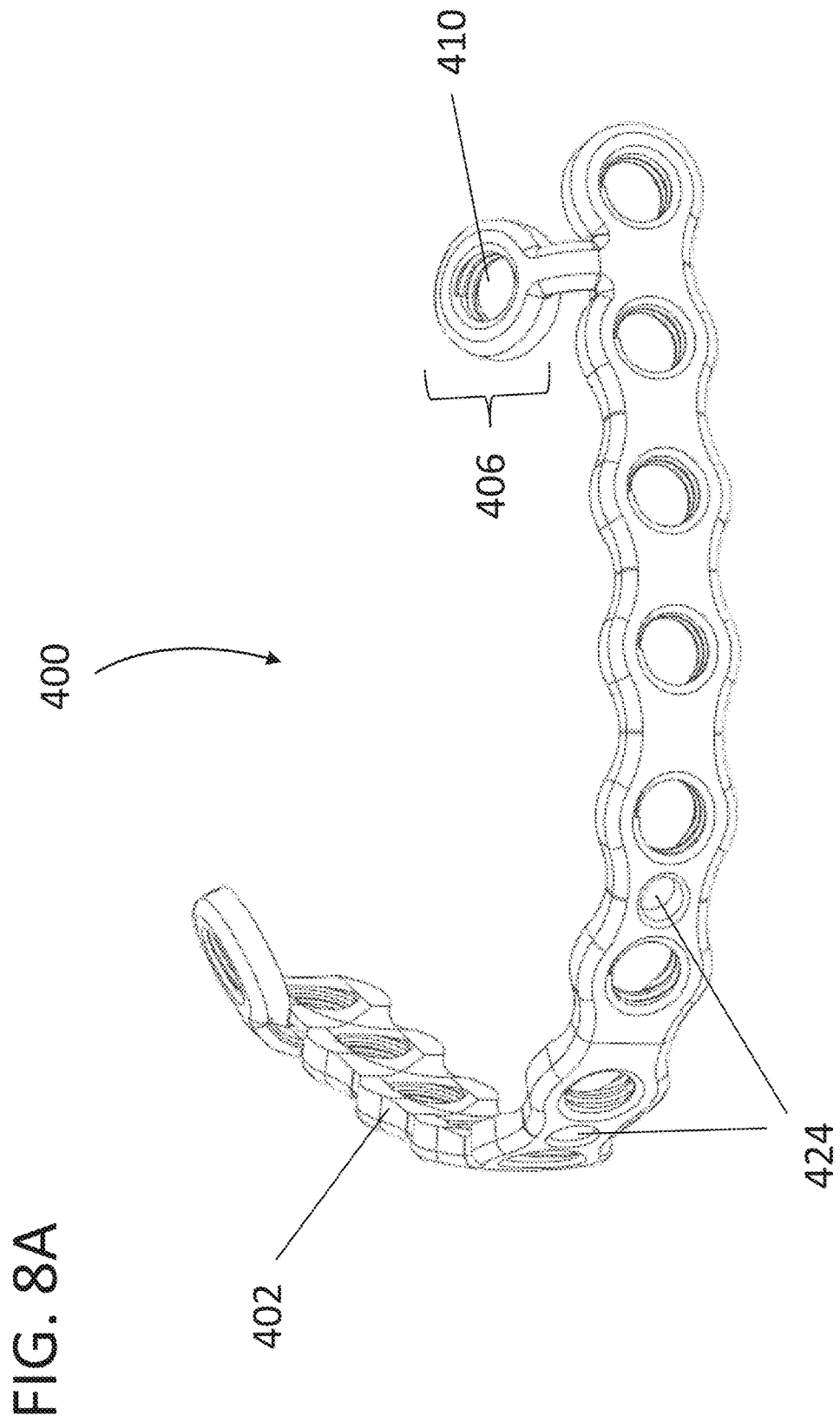
FIG. 8A illustrates a perspective view of a fracture reduction device, in accordance with at least one example of the present disclosure.
Figure 8B:
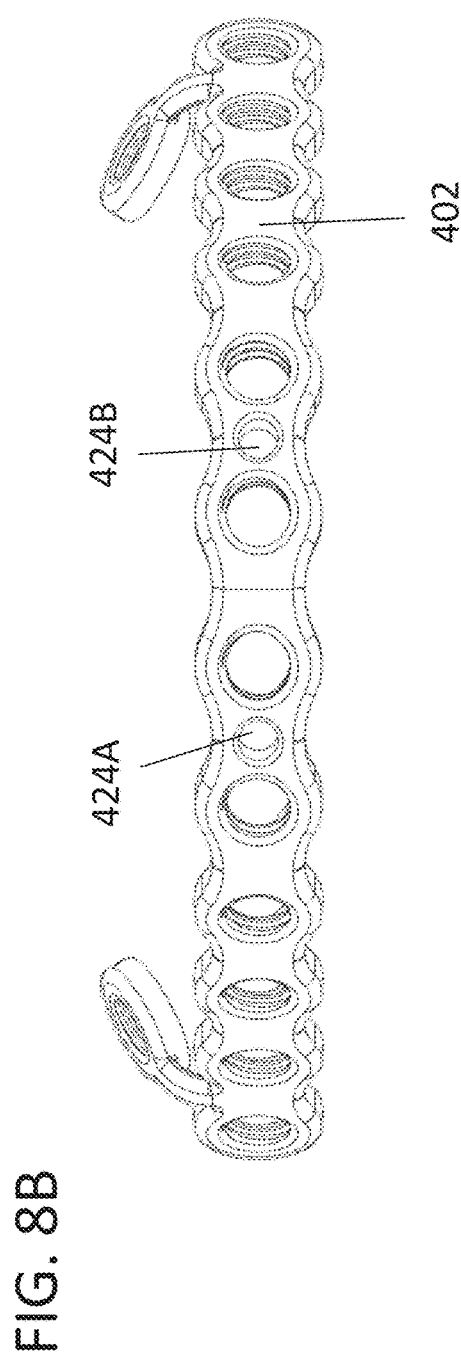
FIG. 8B illustrates a side view of a fracture reduction device, in accordance with at least one example of the present disclosure.
Figure 8C:
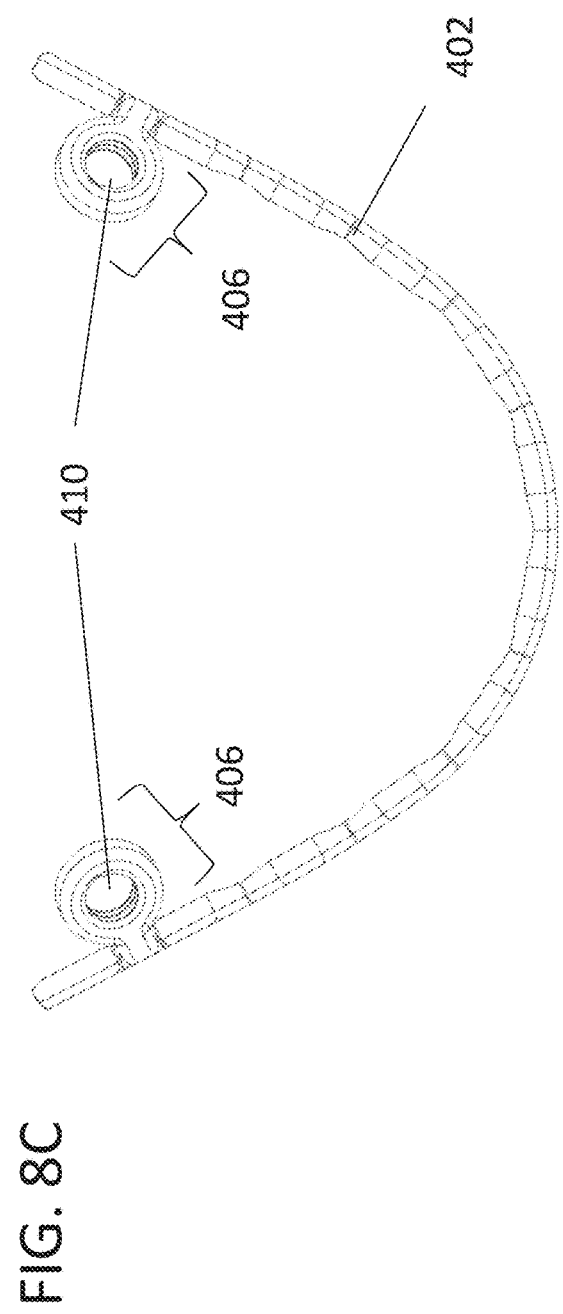
FIG. 8C illustrates a top view of a fracture reduction device, in accordance with at least one example of the present disclosure.

In another example, as illustrated in FIGS. 8A-8C, a fracture reduction device 400 comprising a plate 402 can include at least two anchor holes 424, such as anchor holes 424a and 424b. FIGS. 8A-8C further illustrate that the plate 402 can also include selectively removable tabs 406 as described above with respect to tabs 106. At least one of the tabs 406 can include a tab attachment hole 410 disposed therein. Alternatively, multiple or each of the tab members 406 can include a tab attachment hole 410 disposed therein. Tab attachment hole(s) 410 can accept a securing element.

In an example illustrated in FIG. 9, a fracture reduction device having anchor holes disposed therein (e.g. device 400) can be secured at least partially via a wire to the patella to aid in fracture reduction. Here, wire 530 can be routed from the first anchor hole 424a through a first length of the patella $L_1$ along a first path. The wire 530 can be positioned along an exterior length of the perimeter of the patella $L_2$. The exterior length of the perimeter of the patella $L_2$ can be positioned on the opposite side of the patella 540 from the plate 402. The wire 530 can further be routed through a second length of the patella $L_3$ along a second path and secured to the second anchor hole 424b. The wire 530 can be tensionable to aid in reduction of the patella fracture.

Alternatively, other types of securing devices can be used to secure the anchor holes to the patella. For example, the anchor holes can be configured to receive sutures that can be secured to the patella and to the anchor holes to create tension across the patella fracture. Additionally or alternatively, the anchor holes can be used to anchor a braided fixation system, for example, a braided polyethylene fixation system such as the Zimmer Biomet ZipLoop™ Technology (Zimmer Biomet, Warsaw, Ind.) that creates tension with an opposing edge of the patella.

VARIOUS NOTES & EXAMPLES

Example 1 is a device that can comprise a patellar plate body that can be formed from a monolithic material and can comprise a central portion and a peripheral portion at least partially surrounding the central portion. The central portion including a plurality of plate attachment holes disposed therein, and the peripheral portion can comprise a plurality of tabs. Each tab can be coupled to the central portion via a connector portion that has a thickness that is less than about 80% of a plate thickness of the patellar plate body. Each tab can include a tab attachment hole disposed therein. Each tab can be selectively detachable from the patellar plate body. The patellar plate body can be sized in at least a horizontal and a vertical direction to fit a patella.

In Example 2, the subject matter of Example 1 can optionally include the central portion comprising a pentagonal shape.

In Example 3, the subject matter of any one or more of Examples 1-2 can optionally include one plate attachment hole or one tab attachment hole than can accept a screw having a diameter of between about 2.0 mm and about 3.0 mm.

In Example 4, the subject matter of any one or more of Examples 1-3 can optionally include wherein the plate body includes at least six attachment holes.

In Example 5, the subject matter of any one or more of Examples 1-4 can optionally include wherein the plate body includes at least eight attachment holes.

In Example 6, the subject matter of any one or more of Examples 1-5 can optionally include wherein the monolithic material comprises titanium or a titanium alloy.

In Example 7, the subject matter of any one or more of Examples 1-6 can optionally include wherein the patellar plate body is less than about 3.0 mm thick.

In Example 8, the subject matter of any one or more of Examples 1-7 can optionally include wherein the patellar plate body is less than about 2.0 mm thick.

In Example 9, the subject matter of any one or more of Examples 1-8 can optionally include wherein the patellar plate body is less than about 1.6 mm thick.

In Example 10, the subject matter of any one or more of Examples 1-9 can optionally include wherein each of the plate attachment holes further comprises a guide insert for aiding in initially securing the patellar plate body to the patella prior to a securing element being inserted through a respective one of the plate attachment holes.

In Example 11, the subject matter of Example 10 can optionally include wherein the guide insert is removable prior to inserting the securing element through the respective one of the plate attachment holes.

In Example 12, the subject matter of any one or more of Examples 1-11 can optionally include wherein the securing element is a locking screw or a non-locking screw.

Example 13 is a device comprising: a curved perimeter plate contoured to a perimeter of substantially any patella and defining a plate length between a first end and a second end thereof that extends along at least a portion of the perimeter of a patella, the perimeter plate comprising a plurality of connection regions positioned along the plate length and a plurality of securing regions positioned along the plate length, wherein at least some of the connection regions are positioned between two adjacent securing regions, and wherein each securing region includes an attachment hole disposed therein.

In Example 14, the subject matter of Example 13 can optionally include wherein the curved perimeter plate extends along at least about one-fifth of the perimeter of the patella and less than about one-third of the perimeter of the patella.

In Example 15, the subject matter of any one or more of Examples 13-14 can optionally include wherein the plate extends along at least about one-third of the perimeter of the patella and less than about two-thirds of the perimeter of the patella.

In Example 16, the subject matter of any one or more of Examples 13-15 can optionally include wherein at least one of the securing regions includes an attachment hole that In Example 17, the subject matter of any one or more of Examples 13-16 can optionally include wherein the curved perimeter plate includes at least six attachment holes.

In Example 18, the subject matter of any one or more of Examples 13-17 can optionally include wherein the curved perimeter plate comprises titanium or a titanium alloy.

In Example 19, the subject matter of any one or more of Examples 13-18 can optionally include wherein each of the attachment holes further comprises a guide insert for aiding in initially securing the curved perimeter plate to the patella prior to a securing element being inserted through a respective one of the attachment holes.

In Example 20, the subject matter of Example 19 can optionally include wherein the guide insert is removable prior to inserting the securing element through the respective one of the attachment holes.

In Example 21, the subject matter of any one or more of Examples 13-20 can optionally include wherein the plate further includes at least two anchor holes disposed therein.

In Example 22, the subject matter of Example 21 can optionally include a wire routable from a first anchor hole of the at least two anchor holes through a first length of the patella along a first path disposed along an exterior length of the perimeter of the patella, the exterior length of the perimeter of the patella being positioned on the opposite side of the patella from the plate, and routed back through a second length of the patella along a second path and secured to a second anchor hole of the at least two anchor holes, wherein the wire is selectively tensionable.

Example 23 is a system that can comprise a patellar plate body and a curved perimeter plate. A patellar plate body can be formed from a monolithic material and can comprise a central portion and a peripheral portion at least partially surrounding the central portion. The central portion including a plurality of plate attachment holes disposed therein, and the peripheral portion can comprise a plurality of tabs. Each tab can be coupled to the central portion via a connector portion that has a thickness that is less than about 80% of a plate thickness of the patellar plate body. Each tab can include a tab attachment hole disposed therein. Each tab can be selectively detachable from the patellar plate body. The patellar plate body can be sized in at least a horizontal and a vertical direction to fit a patella. A curved perimeter plate contoured to a perimeter of substantially any patella and defining a plate length between a first end and a second end thereof that extends along at least a portion of the perimeter of a patella, the perimeter plate comprising a plurality of connection regions positioned along the plate length and a plurality of securing regions positioned along the plate length, wherein at least some of the connection regions are positioned between two adjacent securing regions, and wherein each securing region includes an attachment hole disposed therein.

Each of these non-limiting examples can stand on its own, or can be combined in various permutations or combinations with one or more of the other examples. In the examples, the terms "a" and "the" are used interchangeably, such that reference to "the plate" in a given example can refer to a plate described in a previous example that is optionally combined with the given example, or can refer to a separate tether entirely. Similarly "a plate" can refer to a newly introduced plate, or to a plate described in a previous example.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device, comprising:
a patellar plate body formed from a monolithic material and comprising a central portion and a peripheral portion at least partially surrounding the central portion, the central portion including a plurality of plate attachment holes disposed therein, and the peripheral portion comprising a plurality of tabs, each tab coupled to the central portion via a connector portion, each tab being selectively detachable from the patellar plate body, wherein the patellar plate body is sized in at least a horizontal and a vertical direction to fit a patella.

2. The plate of claim 1, wherein the central portion comprises a pentagonal shape.

3. The plate of claim 1, wherein one plate attachment hole or one tab attachment hole accepts a screw having a diameter of between 2.0 mm and 3.0 mm.

4. The plate of claim 1, wherein the plate body includes at least six attachment holes.

5. The plate of claim 1, wherein the plate body includes at least eight attachment holes.

6. The plate of claim 1, wherein the monolithic material comprises titanium or a titanium alloy.

7. The plate of claim 1, wherein the patellar plate body is less than 3.0 mm thick.

8. The plate of claim 1, wherein the patellar plate body is less than 2.0 mm thick.

9. The plate of claim 1, wherein the patellar plate body is less than 1.6 mm thick.

10. The plate of claim 1, wherein each of the plate attachment holes further comprises a guide insert for aiding in initially securing the patellar plate body to the patella prior to a securing element being inserted through a respective one of the plate attachment holes.

11. The plate of claim 10, wherein the guide insert is removable prior to inserting the securing element through the respective one of the plate attachment holes.

12. The plate of claim 10, wherein the securing element is a locking screw or a non-locking screw.

13. The plate of claim 1, wherein the connector portion has a thickness that is less than 80% of a plate thickness of the patellar plate body, each tab including a tab attachment hole disposed therein.

14. A device comprising:
a curved perimeter plate shaped to be contoured to a perimeter of substantially any patella and defining a plate length between a first end and a second end thereof configured to extend along at least a portion of the perimeter of a patella, the curved perimeter plate comprising a plurality of connection regions positioned along the plate length and a plurality of securing regions positioned along the plate length, wherein at least some of the connection regions are positioned between two adjacent securing regions, and wherein each securing region includes an attachment hole disposed therein.

15. The device of claim 14, wherein the curved perimeter plate is configured to extend along at least one-fifth of the perimeter of the patella and less than one-third of the perimeter of the patella.

16. The device of claim 14, wherein the curved perimeter plate is configured to extend along at least one-third of the perimeter of the patella and less than two-thirds of the perimeter of the patella.

17. The device of claim 14, wherein at least one of the securing regions includes an attachment hole that accepts a screw having a diameter of between 2.0 mm and 3.0 mm.

18. The device of claim 14, wherein the curved perimeter plate includes at least six attachment holes.

19. The device of claim 14, wherein the curved perimeter plate comprises titanium or a titanium alloy.

20. The device of claim 14, wherein each of the attachment holes further comprises a guide insert for aiding in initially securing the curved perimeter plate to the patella prior to a securing element being inserted through a respective one of the attachment holes.

21. The reduction device of claim 20, wherein the guide insert is removable prior to inserting the securing element through the respective one of the attachment holes.

22. The device of claim 14, wherein the plate further includes at least two anchor holes disposed therein.

23. The device of claim 22, further comprising a wire routable from a first anchor hole of the at least two anchor holes through a first length of the patella along a first path disposed along an exterior length of the perimeter of the patella, the exterior length of the perimeter of the patella being positioned on the opposite side of the patella from the plate, and routed back through a second length of the patella along a second path and secured to a second anchor hole of the at least two anchor holes, wherein the wire is selectively tensionable.

24. A system, comprising:
a patellar plate body formed from a monolithic material and comprising a central portion and a peripheral portion surrounding the central portion, the central portion including a plurality of patellar plate attachment holes disposed therein, and the peripheral portion comprising a plurality of tabs, each tab coupled to the central portion via a connector portion that is less than 80% of a plate thickness of the patellar plate body, each tab including a tab attachment hole disposed therein, each tab being selectively detachable from the patellar plate body, wherein the patellar plate body is contoured to fit substantially any patella; and
a curved perimeter plate shaped to be contoured to a perimeter of substantially any patella and defining a plate length between a first end and a second end thereof configured to extend along at least a portion of the perimeter of a patella, the curved perimeter plate comprising a plurality of connection regions positioned along the plate length and a plurality of securing regions positioned along the plate length, wherein at least some of the connection regions are positioned between two adjacent securing regions, and wherein each securing region includes a perimeter plate attachment hole disposed therein.

* * * * *